United States Patent [19]

Puhk

[11] Patent Number: 4,699,015
[45] Date of Patent: Oct. 13, 1987

[54] METHOD FOR DETERMINING PARTICLE SIZE AND/OR DISTRIBUTION

[75] Inventor: Heino Puhk, N. Olmsted, Ohio

[73] Assignee: The Glidden Company, Cleveland, Ohio

[21] Appl. No.: 899,868

[22] Filed: Aug. 25, 1986

[51] Int. Cl.⁴ ............................................ G01N 15/00
[52] U.S. Cl. .................................................. 73/865.5
[58] Field of Search ............................. 73/865.5, 61.4

[56] References Cited

U.S. PATENT DOCUMENTS 3,475,968 11/1969 Jones ................................... 73/865.5
4,311,039 1/1982 Koehler et al. ..................... 73/865.5
4,478,073 10/1984 Holsworth et al. ................. 73/865.5

Primary Examiner—Stewart J. Levy
Assistant Examiner—Robert R. Raevis
Attorney, Agent, or Firm—Thomas M. Schmitz

[57] ABSTRACT

There is provided an improved method for particle size and distribution determinations using a photosedimentometer having a centrifugal disc chamber for containing a spin fluid. The spin fluid must be characterized by a density gradient. The present process provides a novel way of composing the spin fluid. The less dense component water/alcohol is introduced first, and the more dense component (e.g., water) is introduced second. At no time is the power to the motor driving the disc interrupted as in prior art methods. Better and more reproducible results are secured.

8 Claims, 6 Drawing Figures

METHOD FOR DETERMINING PARTICLE SIZE AND/OR DISTRIBUTION

This invention relates to a method for analyzing particle size and/or distribution especially in a liquid medium such as latex or a pigment slurry.

BACKGROUND OF THE INVENTION AND PRIOR ART

The disc centrifuge photosedimentometer has proved to be an excellent instrument for providing particle size and particle size distribution information to pigment and latex manufacturers and formulators. In use, a disc centrifuge photosedimentometer operates by forcing particles (generally of less than about 2 microns in size) under high centrifugal force radially outwardly through a spin fluid or medium. Here the particles segregate into sizes, the larger traversing the medium more quickly, and the smaller taking a longer time. In general, bands of particles of approximately the same size are created in the medium and can be measured optically with the aid of light or other suitable radiation to which the particles are opaque, which radiation traverses the spin medium in an axial direction. The bands so created intercept the radiation and can be analyzed and the data obtained converted to particle size and/or distribution curves.

A particularly satisfactory method for photosedimentometric analysis is that described and claimed in U.S. Pat. No. 3,475,968 dated 4 Nov. 1969. U.S. Pat. No. 4,311,039 dated 19 Jan. 1982 describes and claims an apparatus which is especially effective in practicing the method of the aforesaid U.S. Pat. No. 3,475,968. The apparatus of U.S. Pat. No. 4,311,039, with or without "cut timer" modifications, can be used most satisfactorily in practicing the present method. Thus, the disclosure of U.S. Pat. No. 4,311,039 is incorporated herein by reference.

U.S. Pat. No. 4,478,073 dated 23 Oct. 1984 provides a new and alternative method for making centrifugal disc photosedimentometric analyses which also allows simplification in the aforesaid improved apparatus of U.S. Pat. No. 4,311,039, as well as the apparatus of U.S. Pat. No. 3,475,968. Power interrupting means utilized in the devices of both the latter patents can, if desired, be eliminated. In any event, such power interrupting means are not used in practicing the present invention or the invention of U.S. Pat. No. 4,478,073. Moreover, the results obtained according to the new method as will be shown herein, are improved over the results obtained with U.S. Pat. No. 4,478,073 or U.S. Pat. No. 4,311,039 using the buffered line start method described in U.S. Pat. No. 3,475,968 and in the prior art mentioned below. Especially, the improved method of the present invention contemplates the formation of the spin fluid including a density gradient, internally of the disc but without the necessity for interrupting the spinning of the disc in order to generate a necessary density gradient.

Respecting spin fluid media, the homogenous method, the line start, and the buffered line start methods, are all well known. The latter two systems involve preparations of spin fluids or spin media in situ, i.e., during high speed rotation. Reference may be had to Chemical Analysis, "Direct Characterization of Fine Particles" by B. H. Kaye, Volume 61, John Wiley & Sons (1981) Pages 189-226; Schnelle Dichtegradienten-Zentrifugation dispergierter Teilchen, Lange, Colloid & Polymer Sci., 258, p. 1077-1085 (1980) CODEN CPMSS); "Zur Sedimentationsanalyse wassriger Kunkstoffdispersionen mit der Scheibenzentrifuge" Langer, Colloid and Polymer Sci., 257, p. 522-532 (1979) CODEN CPMSE; Zur Genauigkeit der Teilchengrossenanalyse durch Sedimentation im Zentrifugalfeld" Alex, Dissertation for PhD in Engineering 15 Jul 1972 Universitat Kalsruhe. Reference may also be had to the following U.S. Pat. Nos. 2,956,434 Donoghue; 3,237,455 Slater; 3,243,106 Atherton, and the following articles; Jones et al "Particle Size Analysis of Inorganic Pigments" Anal. Chim Acta 38, (1967) 143-146; Proc. Soc. Anal. Chem., Particle Size Analysis Group, July 1966 "The ICI—Joyce Loebl Disc Centrifuge", Jones; Powder Technology, 13 (1976), 215-221 "Particle Size Determination of Pigments with a Disc Centrifuge," Brugger; "Centrifugal Sedimentation, Fraser, Pigments Handbook III-A-d-2-ii, pp. 53-62; "The Accuracy and Precision of the Centrifugal Disc Photosedimentometer Method of Particle Size Analysis", Burt, Powder Technology, 1, (1967) 103-115; "Size Analysis of Organic Pigments using the ICI-Joyce-Loebl Disc Centrifuge", Beresford, Jour. Oil & Color Chem. Assoc. Vol. 50, (1967) 594-614; "The Measurement of Particle Size and its Practical Significance in Vat Dye Quality", Atherton et al, J. Soc. Dyers Colourists 80, p. 521-526 (1964); G. P. Langer, "Sedimentation Analysis of Aqueous Polymer Dispersions with a Disc Centrifuge;" Colloid and Polymer Sci., 257, 522-532 (1979); and Scarlett et al, "The Two Layer Method of Particle Size Analysis", Particle Size Analysis Conference, 1966 pages 242-267.

From the foregoing patents and literature, it will be seen that the industry method of choice is the Joyce-Loebl buffered line start method for particle size determination. Because of its improved structure and control means, the apparatus described and claimed in U.S. Pat. No. 4,311,039 is especially useful in carrying out the buffered line start method.

BRIEF STATEMENT OF THE INVENTION

Briefly stated, the present invention is a method for the determination of size and/or distribution of particles eminating from a mother liquid by sedimentation in a continuously rotating disc centrifuge which comprises the steps of injecting a buffer fluid e.g., a $C_1$-$C_4$ alkanol such as methanol, ethanol, etc. into the disc while the disc is spinning at a predetermined speed. Subsequently, there is injected into the disc while continuing rotation at said predetermined speed, a miscible spin fluid having a density greater than that of said buffered fluid. Thereafter, there is injected into the disc while continuing rotation at the predetermined speed, a mother liquid containing particles the size and/or distribution of which are to be determined. There is no interruption of or change in the speed of or change in the speed of rotation of the disc. Finally, the particle size and/or distribution of the particles in the mother liquid are measured by known means such as those described in the U.S. Pat. No. 3,475,968 to Jones.

Basically, the discovery of the present invention is that by introducing the spin fluid forming liquids, such as those described in the Jones U.S. Pat. No. 3,475,968, in the reverse order from that disclosed in the Jones patent, the density gradient necessary for determination of the particle size and/or distribution can be generated in situ without the need for a "manual cut timer" or an electronically controlled "cut timer" such as disclosed in U.S. Pat. No. 4,311,039, supra.

BRIEF DESCRIPTION OF THE DRAWINGS

The invention may be better understood by having reference to the annexed drawings wherein.

DETAILED DESCRIPTION OF THE INVENTION

Figure 1:
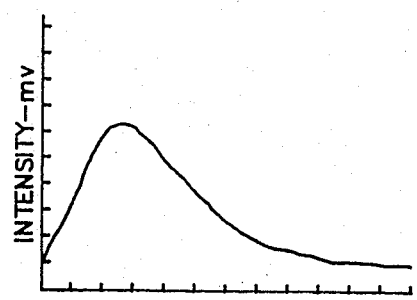
FIG. 1 is a particle size trace obtained using the apparatus of U.S. Pat. No. 4,311,039, and the process described therein employing the highly accurate "cut timer".

As indicated above, the present invention is an improvement on the buffered line start method described and claimed in the U.S. Pat. No. 3,475,968 to Jones. Reduced to its simplest terms, the invention contemplates the introduction of the liquid ingredients which form the "spin fluid" into the rotating disc in an order which is the reverse of that disclosed in the aforesaid Jones patent. In other words, instead of introducing a more dense liquid as the first addition to the rotating disc followed by the addition of a less dense liquid, and then followed by the timed interruption of the application of power to the rotating disc to establish within the "spin fluid" a density gradient, the present invention contemplates the introduction of first a less dense buffer solution into the rotating centrifuge disc followed by the introduction of a more dense spin fluid forming material, and omitting the step of interrupting the application of power to the motor driving the disc. A primary problem with the apparatus used in practicing the so called "buffered line start" method according to the Jones patent, supra., was that the power interruption step was manually effected. This introduced errors in that the duration of the period during which power was cut off from the driving motor varied from run to run causing great difficulty in obtaining reproducible results.

This problem was solved in the Koehler et al U.S. Pat. No. 4,311,039 dated 19 Jan. 1982, above referred to. In this case, the "buffered line start" method was used, but the apparatus was provided with an electronically accuated "cut timer" together with other apparatus which enabled very precise control of the speed of rotation of the disc and the interval during which power was removed from the driving motor. This enabled reproducible results to be obtained.

The present invention differs from the two foregoing inventions is that the order of introduction the fluids is reversed. These fluids have different densities. The fluid of heavier density is introduced after the fluid of less density, and under the influence of the relatively high speed rotation of the disc, the more dense fluid begins to flow outwardly through the less dense fluid forming a density gradient. Such density gradient is, as explained in the Jones Patent, supra. essential to the success of the method for determining particle size and/or distribution. In accordance with the present invention, however, and contrary to the two previously discussed procedures using the "buffered line start" method, no "cut timer" or manual interruption of the power to the driving motor is needed to initiate the formation of a density gradient within the spin fluid.

This change simplifies the apparatus, makes it much less expensive, and facilitates the making of measurements. The reproducibility of results is also improved as will appear from the following specific examples with reference to the annexed drawings.

In a typical case, the method of the present invention involves injecting a predetermined amount (1 ml) of a less dense buffer solution, for example, (a 50% water-methanol solution) into a rotating centrifuge disc, followed by the injection of a larger quantity (15 ml) of a more dense spin fluid, e.g., water. The rotation of the centrifuge disc is maintained constant throughout the entire conduct of the test from the time the first less dense buffered solution is introduced to the time the test solution or dispersion is added and the measurements taken. While the disc is rotating, a density gradient is formed in situ because of the tendency of the denser fluid to move into the less dense buffered solution. Thereafter, a mother liquid containing the particles to be measured is injected into the rotating centrifuge disc. These particles have a size generally in the range of from about 2000 Å to about 8000 Å. The particles diffuse outwardly in proportion to their size, and the particle sizes and distribution are then computed. As indicated in the previous references, the particles distribute themselves within the spin fluid in accordance with their size, generally in the form of bands which traverse the spin fluid and interrupt a light beam passing through the fluid in an axial direction. The change in intensity of the light can be detected. FIGS. 1 to 5 in the annexed drawings are graphs showing the variation of the intensity of the light beam with time and thus giving a measure of the particle size and distribution thereof.

SPECIFIC EXAMPLES

In the following specific examples, various methods of determining particle size and/or distribution have been compared using the same piece of apparatus, the same test latex and the same spin fluid forming ingredients. All tests are conducted using the same centrifugal disc rotating at the same predetermined speed.

The buffer solution of less density was a 50% aqueous solution of methanol and demineralized water. A trace [0.15%] of Triton X-100 surfactant (alpha-[4-(1,1,3,3-tetramethylbutyl)phenyl]omega-hydroxy-poly(oxy-1,2-ethanediyl) having Chemical Abstracts Registry No. 9002-93-1 may optionally be added. The spin fluid amounting to 15 milliliters, was composed of demineralized water also with or without the same amount of the same surfactant. The test liquid contained from 3 to 20 drops of vinyl acetate-butyl acrylate copolymer latex in 25 ml of 50% aqueous methanol. In preparing this test liquid, the dispersion is agitated by sonic means for a period of 5 minutes and immediately introduced into the rotating cavity. Computerized data are then evaluated. Such computerized data are represented in FIGS. 1 to 5 and annexed hereto.

In the annexed drawings, the abscissa is divided into units representing minutes. The ordinant is divided into units representing intensity of light in volts.

FIG. 1 represents the trace obtained when light intensity in volts is plotted against time in minutes utilizing the electronic cut timer apparatus described and claimed in U.S. Pat. No. 4,311,039 and the "buffered line start method" described in U.S. Pat. No. 3,475,968.

Figure 2:
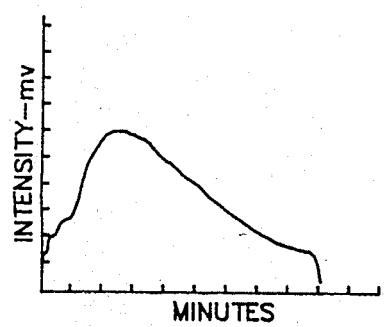
FIGS. 2 and 3 are replicative traces obtained using the externally generated gradient method described and claimed in U.S. Pat. No. 4,478,073.
Figure 3:
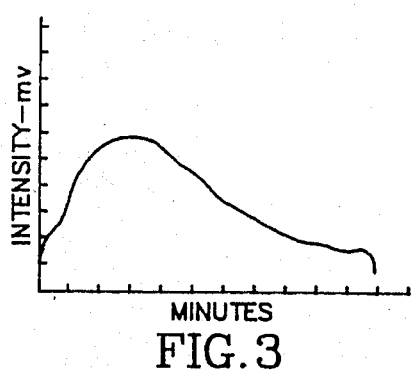

FIGS. 2 and 3 are replicative examples showing the traces obtained utilizing the external gradient method described and claimed in U.S. Pat. No. 4,478,073.

Figure 4:
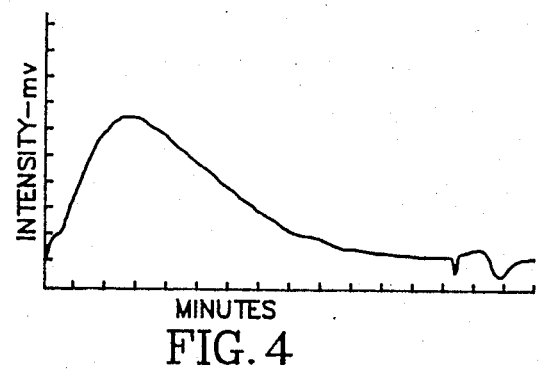
FIGS. 4 and 5 are replicative examples showing traces obtained using the method of the present invention.
Figure 5:
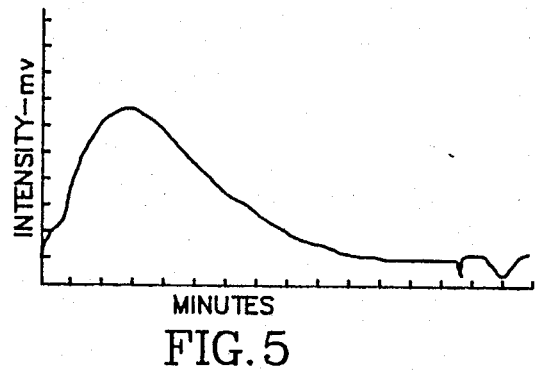

FIGS. 4 and 5 are replicative examples showing the traces obtained utilizing the method of present invention, and illustrating particularly the stability of the base line.

Figure 6:
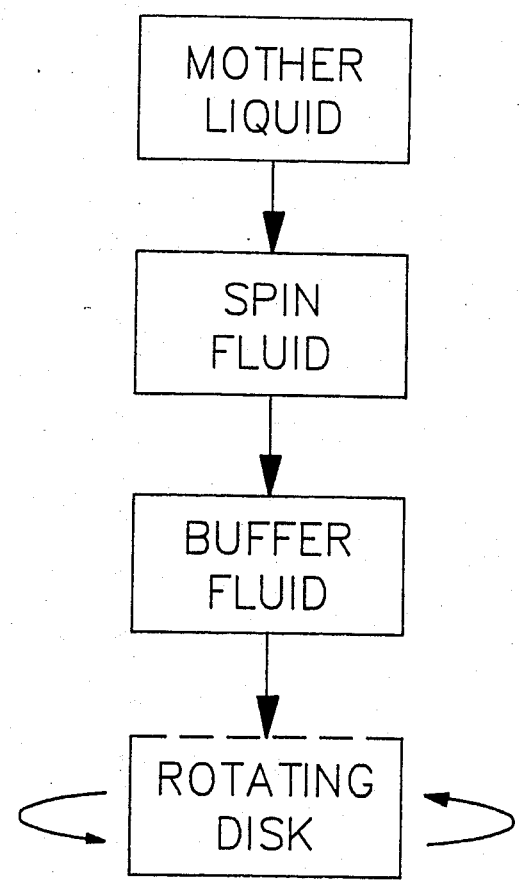
FIG. 6 is a diagrammatic flow chart showing the order of introduction of the various fluids into the rotating disc.

FIG. 6 shows in diagrammatic form a flow chart illustrating the order of addition of the fluids to the rotating disc.

Referring to the trace obtained in FIG. 1, the data obtained in this run were as follows:

| PARTICLE SIZE ANALYSIS | |
|---|---|
| Weight Average (Mircon) | .4473 |
| Number Average (Micron) | .3192 |
| Surface Average (Micron) | .3628 |
| Polydispersity | 1.4013 |
| SAMPLE PARAMETERS | |
| Example No. (FIG. 1) | 1 |
| Disc RPM | 3585 |
| Particle Density (grams/ml) | 1.1440 |
| Low Diameter (Micron) | .1910 |
| High Diameter (Micron) | 2.5625 |
| Area Under Curve | 10.24 |
| SPIN FLUID | |
| Temperature (°C.) | 25.1 |
| Volume (ml) | 15.0 |
| Density (grams/ml) | .9970535 |
| Viscosity (Poise) | .0088844 |
| BASELINE PARAMETERS | |
| Slope | −.0004 |
| Intercept | .124 |
| Starting Value (v) | .124 |
| Ending Value (v) | .101 |
| First Data Point (min) | .33 |
| Last Data Point (min) | 60.00 |

The data for FIGS. 2 and 3 were obtained using the externally generated spin fluid method as above described.

FIG. 2 has the following data:

| PARTICLE SIZE ANALYSIS | |
|---|---|
| Weight Average (micron) | .4518 |
| Number Average (micron) | .3135 |
| Surface Average (micron) | .3555 |
| Polydispersity | 1.4386 |
| SAMPLE PARAMETERS | |
| Example No. (FIG. 2) | 2 |
| Disc RPM | 3585 |
| Particle Density (g/ml) | 1.1400 |
| Low Diameter (micron) | .2242 |
| High Diameter (micron) | 2.9625 |
| Area Under Curve | 10.99 |
| SPIN FLUID | |
| Temperature (C.) | 25.0 |
| Volume (ml) | 15.0 |
| Density (g/ml) | .9970791 |
| Viscosity (Poise) | .0089047 |
| BASELINE PARAMETERS | |
| Slope | −.0000 |
| Intercept | .108 |
| Starting Value (v) | .108 |
| Ending Value (v) | .106 |
| First Data Point (min) | .25 |
| Last Data Point (min) | 43.67 |

FIG. 3 has the following data:

| PARTICLE SIZE ANALYSIS | |
|---|---|
| Weight Average (micron) | .4417 |
| Number Average (micron) | .3020 |
| Surface Average (micron) | .3491 |
| Polydispersity | 1.4625 |
| SAMPLE PARAMETERS | |
| Example No. (FIG. 3) | 3 |
| Disc RPM | 3586 |
| Particle Density (g/ml) | 1.1400 |
| Low Diameter (micron) | .2057 |
| High Diameter (micron) | 2.9617 |
| Area Under Curve | 10.48 |
| SPIN FLUID | |
| Temperature (C.) | 25.0 |
| Volume (ml) | 15.0 |
| Density (g/ml) | .9970791 |
| Viscosity (Poise) | .0089047 |
| BASELINE PARAMETERS | |
| Slope | −.0001 |
| Intercept | .102 |
| Starting Value (v) | .102 |
| Ending Value (v) | .097 |
| First Data Point (min) | .25 |
| Last Data Point (min) | 51.83 |

The data resulting in the traces of FIGS. 4 and 5 are as follows:

FIG. 4 has the following data:

| PARTICLE SIZE ANALYSIS | |
|---|---|
| Weight Average (micron) | .4358 |
| Number Average (micron) | .3016 |
| Surface Average (micron) | .3466 |
| Polydispersity | 1.4451 |
| SAMPLE PARAMETERS | |
| Example No. (FIG. 4) | 4 |
| Disc RPM | 3585 |
| Particle Density (g/ml) | 1.1400 |
| Low Diameter (micron) | .1835 |
| High Diameter (micron) | 2.9589 |
| Area Under Curve | 12.41 |
| SPIN FLUID | |
| Temperature (C.) | 25.1 |
| Volume (ml) | 15.0 |
| Density (g/ml) | .9979535 |
| Viscosity (Poise) | .0088844 |
| BASELINE PARAMETERS | |
| Slope | −.0000 |
| Intercept | .103 |
| Starting Value (v) | .103 |
| Ending Value (v) | .102 |
| First Data Point (min) | .25 |
| Last Data Point (min) | 65.00 |

FIG. 5 has the following data:

| PARTICLE SIZE ANALYSIS | |
|---|---|
| Weight Average (micron) | .4433 |
| Number Average (micron) | .3034 |
| Surface Average (micron) | .3499 |
| Polydispersity | 1.4614 |
| SAMPLE PARAMETERS | |
| Example No. (FIG. 5) | 5 |
| Disc RPM | .3585 |
| Particle Density (g/ml) | 1.1400 |
| Low Diameter (micron) | .1833 |
| High Diameter (micron) | 2.9553 |
| Area Under Curve | 13.02 |
| SPIN FLUID | |
| Temperature (C.) | 25.2 |
| Volume (ml) | 15.0 |
| Density (g/ml) | .9970278 |
| Viscosity (Poise) | .0088643 |
| BASELINE PARAMETERS | |
| Slope | 0.0000 |
| Intercept | .097 |
| Starting Value (v) | .097 |
| Ending Value (v) | .097 |

-continued

| | |
|---|---|
| First Data Point (min) | .25 |
| Last Data Point (min) | 65.00 |

It will be observed in Examples 4 and 5 that the last data point in each case was obtained at from 65 to 66 minutes. This indicates a long base line and therefore, greater accuracy at the point of fall off. The deep depression in the curve in each of FIGS. 4 and 5 at the tail end is to believed to have been caused by evaporation of methanol from the rotating disc.

The following tables compare the three methods illustrated above in FIG. 1, FIGS. 2 and 3, and FIGS. 4 and 5 in terms of the time required to form a suitable base line and also in terms of the standard deviation in replicative results.

It has been found that improved results are obtained when a small amount of a relatively high boiling hydrocarbon η or other organic material insoluble in the spin medium, e.g., dodecane, is injected into the disc while it is spinning, on the top of the buffer-spin fluid system, equilibrated, and the latex sample injected on top of the dodecane. The use dodecane gives better results and provides, therefore, the best mode of carrying out the present invention. The use of dodecane in connection with the buffered line start method has been disclosed in an article entitled "Improved Techniques in Disk Centrifugation" by Hans Coll and Larry E. Oppenheimer at the Research Laboratories of Eastman Kodak Company in Rochester, N.Y. These workers found that the results obtained from disc centrifuge particle size determinations have been improved substantially by using preformed density gradients in the rotor fluid rather than the commonly used buffer-layer method, by protecting the fluid from evaporative cooling with a thin oil layer and by proper correction of the optical signal with the help of light scattering theory. It has been found by these workers that the oil-covered density gradient in the rotor is stable for hours and even at high rotor speeds. Several samples can often be injected consecutively into the same spin fluid gradient with no degradation in the results. Size distributions of spherical and near spherical particles have been determined with great precision. The centrifugation method has been adapted for determining the higher dynamic thickness of polymer layers (such as gelatin) adsorbed onto colloidal particles. More recently, particle size analysis has been extended to nonspherical particles and to nonaqueous media. The advantages of the use of an immiscible organic liquid, e.g., dodecane have been found especially applicable to the new method wherein the spin fluid is internally prepared with the exception that the material of lower density is introduced first, the spin fluid (water) is introduced second, the hydrocarbon, e.g., dodecane, is introduced third and finally the latex sample introduced on top of this spin fluid system.

The following table shows the results obtained comparing the various procedures; the cut timer method, the externally generated spin fluid procedure, and the internally generated spin fluid system of the present invention. The designations "cut", HP, EG, HP12 and EG12 are utilized in the following table. HP represents the present invention, "cut" represents the invention utilizing the apparatus described in U.S. Pat. No. 4,311,039 and the designation EG represents the external gradient method described in U.S. Pat. No. 4,478,073. The numeral 12 following the designation indicates that dodecane was applied as a nonmiscible covering layer.

TABLE I

| Example Number | Latex Number | Method | Disc. Speed rpm | Wt. Avg. Diam. Å | Å | % | Baseline Quality | Minutes to Establish |
|---|---|---|---|---|---|---|---|---|
| 1 | K1625 | Cut | 3586 | 3226 | — | — | Excellent | 48 |
| 2 | K1625 | EGM | 3586 | 3399 | +173 | +5.4 | OK | 40–42 |
| 3 | K-1625 | HP | 3586 | 3188 | −38 | −1.2 | Excellent | 63 |
| 4 | K-1660(1) | Cut(FIG. 1) | 3586 | 4473 | — | — | Excellent | 61 |
| 5 | K-1660(1) | EMG(FIG. 2) | 3586 | 4510 | +37 | +0.8 | Early | 42–44 |
| 6 | K-1660(1) | EGM(FIG. 3) | 3586 | 4417 | −56 | −1.3 | OK | 48–52 |
| 7 | K-1660(1) | HPM(FIG. 4) | 3586 | 4358 | −115 | −2.6 | Excellent | 65 |
| 8 | K-1660(1) | HPM(FIG. 5) | 3586 | 4433 | −40 | −0.9 | Excellent | 65 |
| 9 | K-1660(2) | Cut | 3586 | 5560 | — | — | Excellent | 62 |
| 10 | K-1660(2) | EGM | 3586 | 5651 | +91 | +1.6 | Early | 42–44 |
| 11 | K-1660(2) | EGM | 3586 | 5298 | −262 | −4.7 | Good | 66–69 |
| 12 | 10377-7A | Cut | 6025 | 1718 | — | — | Early | 44–48 |
| 13 | 10377-7A | EGM | 6025 | 1852 | +134 | +7.8 | Early | 28 |
| 14 | 10377-7A | HPM | 6025 | 1610 | −108 | −6.3 | Early | 37 |
| 15 | 10.77-7A | Cut | 6025 | 1754 | — | — | Early | 41 |
| 16 | 10377-7A | EGM | 6025 | 1789 | +35 | +2.0 | Early | 35 |

Mean % + Standard Deviation
HPM = −2.75 ± 2.48
EGM = +1.66 ± 4.12

The following work was done to compare the effects of the addition of 1 ml of dodecane to the spin fluid prior to addition of the test latex in the HPM (the method of the present invention), and the EGM, or external gradient method of U.S. Pat. No. 4,478,073 dated 23 Oct. 1984. The additional notation "C12" indicates tests with dodecane added. After addition of the dodecane, the system is equilibrated for about 5 minutes at disc speed. The following data indicate that the addition of dodecane improves the results of the EGM and the HPM and constitutes, therefore, the best mode of carrying out my invention.

The K-1660(1) and K-1660(2) are different batches of the same latex which is a 57.5% solids dispersion of vinyl acetate-butyl acrylate copolymer (80:20). This latex is a difficult latex to control in production and difficult to make particle size and distribution determinations on. Latices in general having solids contents of from 20% to 60% are useful in forming mother liquids by addition of a few drops (1-30, preferably 2-5 drops) of the latex to demineralized water. Any latex may be tested in accordance with the procedure hereof. Also any dispersion of solids particles in a liquid medium may be tested in accordance herewith, e.g., pigments such as TiO$_2$, metals, such as copper, etc., dispersed in water.

TABLE II

| Standard Deviation K1660(1) latex in Angstroms | | | | |
|---|---|---|---|---|
| HPMC12 | EGMC12 | Cut | HPM | EGM |
| 54 | 57 | 215 | 394 | 1216 |

HPMC12 has a slight advantage over the external gradient method with dodecane, and in a series of runs, the values in HPMC12 and EGMC12 ranged from 25–105 Å.

TABLE III

Methanol Peak. Methanol is part of the spin fluid but gives a peak under certain conditions. This may be a thermal peak due to evaporation. This table shows the time of appearance in minutes of the methanol peak for three latices:

| LATEX | HPMC12 | EGMC12 | HPM | CUT | EGM |
|---|---|---|---|---|---|
| K-1660(1) | None | None | 50 | 60 | 32 |
| K-1660(2) | None | None | 61 | 54 | — |
| 10377 | None | None | None | 55 | 21 |

Dodecane prevents the appearance of a methanol peak.

TABLE IV

Baseline Values: Average baseline values for three latices (vinyl acetate-butyl acrylate 80:20) in decreasing order, in minutes:

| LATEX | METHOD | TIME | METHOD | TIME | METHOD | TIME | METHOD | TIME | METHOD | TIME |
|---|---|---|---|---|---|---|---|---|---|---|
| K-1660(1) | HPMC12 | 72 | EGMC12 | 62 | Cut | 62 | HPM | 50 | EGM | 50 |
| K-1660(2) | HPMC12 | 65 | HPM | 63 | EGMC12 | 57 | Cut | 57 | — | — |
| 10377 | Cut | 67 | HPMC12 | 41 | EGMC12 | 40 | HPM | 38 | EGM | 21 |

Note the longer baselines for HPMC12 than EGMC12.

TABLE V

| | Particle Sizes: | | | | | |
|---|---|---|---|---|---|---|
| LATEX | METHOD SIZE Å | METHOD SIZE Å | METHOD SIZE Å | METHOD SIZE Å | METHOD SIZE Å | C-12 ΔÅ/% |
| K1660(1) | HPMC12 4740 | Cut 5060 | EGMC12 5150 | HPM 5310 | EGM 6800 | 410/8.7 |
| K1660(2) | HPMC12 3950 | HPM 3980 | Cut 4000 | EGMC12 4150 | | 200/5.1 |
| 10377 | Cut 1550 | HPM 1570 | HPMC12 1670 | EGMC12 1760 | EGM 1900 | 90/5.4 |

All EGMC12 values are higher than HPMC12 values because of the shorter base line of the EGMC12 runs. The particle size difference for latices up to 4000Å is 5% and at 5000Å it is 9%.

It is concluded from the foregoing tables that the HPMC12 method is preferred to the cut timer method and to the EGMC12 method.

The foregoing tables and examples have been illustrated utilizing a 50:50 mixture of methanol and deionized water as the buffer or low density solution, and deionized water as the fluid of higher density. Many other materials may be used to form the liquid ingredients of the spin fluid to contact particle size and distribution determinations.

The following are specific examples of spin fluids which may be formed in situ with the aid of an ordinary hypodermic syringe by carefully injecting to the rotating disc the less dense liquid first followed by the liquid or liquids in the order of increasing density. In the preparation of the spin fluids hereof, it is desirable that the viscosities ($\eta$) of the respective liquids should be relatively close, i.e., different from each other by less than about 1 poise at 20° C. Thus, glycerine, with a viscosity of 20° C. of about 8.5 poise and water with a viscosity of about 0.01 poise do not of themselves form a satisfactory spin fluid. The difference in viscosities is too great. However, a glycerine/water solution can be used with a different glycerol/water solution containing a different concentration of glycerol, or with water or an alcohol or a glycol, for example, so long as the viscosities of the liquids differ preferably by less than 1 poise. In the preparation of the in situ spin fluids hereof, the liquid of lower density is preferably injected into the spinning disc cavity followed by the liquid of higher density.

EXAMPLE I

| Water | 11 ml |
|---|---|
| Water 9 ml + MeOH 1 ml (100%) | 10 ml |

EXAMPLE II

| Water | 20 ml |
|---|---|
| MeOH (100%) | 1 ml |

EXAMPLE III

| Water | 5 ml |
|---|---|
| MeOH (100%) | 1 ml |

EXAMPLE IV

| Ethylene glycol | 5 ml |
|---|---|
| Water | 1 ml |

EXAMPLE V

| Ethylene glycol | 5 ml |
|---|---|
| Water | 5 ml |
| MeOH (100%) | 1 ml |

EXAMPLE VI

| Water | 9 ml |
|---|---|
| MeOH (100%) | 1 ml |

The liquid compositions given above are preferred spin fluids. As indicated many other liquid compositions may be used in forming the spin fluids having sn ex situ formed density gradient. Examples of these, many of which are in the prior art in connection with in situ formed density gradients, include:

Glycerol/Water—Water (varied ratios 1:20 to 20:1).
Water—Methanol/water (varied ratios 1:20 to 20:1).
Sucrose/Water—Water (varied ratios 1:20 to 20:1).
Water/Thickener (such as Cellosize)—Ammonium Polymethacrylate (varied ratios 1:20 to 20:1).
Mineral Oil/Solvent—Solvent (varied ratios 1:20 to 20:1).
$CCl_4$/Mineral Spirits—$CCl_4$ (varied ratios 1:20 to 20:1).
Isopropanol/$CCl_4$—Isopropanol (varied ratios 1:20 to 20:1).
Isopropanol/Hexane—Hexane (varied ratios 1:20 to 20:1).
Soluble Resin/Solvent—Solvent (varied ratios 1:20 to 20:1).
Examples from H. Lange; Colloid & Polymer Sci. 258, 1077-1085 (1980).
95 Vol. % $D_2O$—5 Vol. % $H_2O$
94.8 Vol. % Ethylene Glycol—5.2 Vol. % 3-Butene-2-ol.
$H_2O$/Methanol—$D_2O$/Methanol (0-100%).
$H_2O$/Glycerine—$D_2O$/Glycerine (0-100%).
Examples from G. P. Langer; Colloid & Polymer Sci. 257, 522-532 (1979).
12.6 Wt. % Glycerine/$H_2O$—2.38 Wt. % Glycerine/$H_2O$.

EXAMPLES FROM THESIS OF WULF ALEX

Glycerol/$H_2O$—Glycerol/Water 0.13 parts by wt. $C_3H_8O_3$ 19 ml $H_2O$—0.45 parts by wt. $C_3H_8O_3$/21 ml $H_2O$.

It will be seen that the liquids used may vary widely. The principal considerations are that the liquids of the liquid pair or liquid series have different densities at ordinary temperatures and be miscible. It is also desirable that the viscosities of the respective liquid compounds used in forming the spin fluid, or the liquid mixtures used in forming the spin fluids, differ from each other by less than 1 poise at 20° C. Thus, the liquids of a liquid pair, for example, may be fully mixed solutions of the same liquid or solid solute in a solvent, but at different concentrations.

The in situ formed spin fluid containing incompletely mixed liquids of different density and the sample fluid or mother liquid are separately and sequentially in the order named injected into the central part of the disc while spinning at the predetermined speed. A preferred manner of injecting such liquids into a disc centrifuge is clearly set forth in the book by Brian H. Kaye entitled "Direct Characterization of Fine Particles" in the Chemical Analysis Monograph, Volume 61, published by John Wiley & Sons (1981), pp. 189-226, particularly at page 204. The recommended method utilizes a hypodermic needle and syringe to inject the liquids forming the spin fluid and the mother liquid or sample containing the particles in suspension, directly onto the back surface of the rotating centrifuge chamber. By causing the fluids to enter at or near the axis of the disc where the actual linear motion of the system is low, the fluid is able to flow over the back surface and up to the vortex without invading the vortex of the spin fluid. The smallest hypodermic needle compatible with the particles undergoing analysis is recommended.

To test a commercial production batch of 50% solids latex, a couple of drops of the latex in a 20 to 25 ml., volume of 50:50 MeOH/water solution is conveniently used as a mother liquid. The same procedure used in developing the profiles shown in FIGS. 2, 3, 4, 5 and 6 with known particle sizes is used with the unknown samples. The elapsed time to a peak is correlated thru application of Stokes' Law to determine particle size. The shape and elevation of the peak is correlated with distribution. These correlations are described in detail in the prior art mentioned above and thus are known to those skilled in the art.

What is claimed is:

1. A method for analysis of the size and/or distribution of particles emanating from a mother liquid by sedimentation in a continuously rotating disc centrifuge which comprises the steps of injecting a buffer fluid into said disc while said disc is spinning at a predetermined speed, subsequently injecting into said disc while continuing rotation at said predetermined speed, a miscible spin fluid having a density greater than that of said buffer fluid, and thereafter injecting into said disc while continuing rotation at said predetermined speed, said mother liquid containing particles the size and/or distribution of which are to be determined, there being no interruption of or change in the speed of rotation of said disc, and measuring by centrifugal sedimentation the particle size and/or distribution of particles in said mother liquid.

2. A method as defined in claim 1 wherein the buffer fluid is a $C_1$-$C_4$ alkanol in water.

3. A method as defined in claim 2 wherein the alkanol is methanol.

4. A method as defined in claim 2 wherein the alkanol is ethanol.

5. A method as defined in claim 1 wherein the spin fluid is covered with a layer of an immiscible organic liquid.

6. A method as defined in claim 5 wherein the organic liquid is a normally liquid hydrocarbon containing from 6 to 14 carbon atoms.

7. A method as defined in claim 6 in which the hydrocarbon is dodecane.

8. A method as defined in claim 1 wherein the mother liquid is formed of from 1 to 30 drops of a 20% to 60% solids latex having an average particle size in the range of from about 2000 Å to about 8000 Å.

* * * * *